US005806516A

United States Patent [19]
Beattie

[11] Patent Number: 5,806,516
[45] Date of Patent: Sep. 15, 1998

[54] ENDOTRACHEAL TUBE STABILIZER

[76] Inventor: Kathy Beattie, P.O. Box 540222, North Salt Lake, Utah 84054-0222

[21] Appl. No.: 826,242

[22] Filed: Mar. 27, 1997

[51] Int. Cl.[6] ................................................... A61M 25/01
[52] U.S. Cl. ............................... 128/207.17; 128/207.14; 128/911; 128/912; 128/DIG. 26
[58] Field of Search .......................... 128/204.18, 205.11, 128/207.14, 207.18, 207.17, 206.25, 200.26, DIG. 26, 911, 912

[56] References Cited

U.S. PATENT DOCUMENTS

| 4,249,529 | 2/1981 | Nestor et al. | 128/207.17 |
|---|---|---|---|
| 4,502,478 | 3/1985 | Lifton | 128/200.26 |
| 4,744,358 | 5/1988 | McGinnis | 128/207.17 |
| 4,832,019 | 5/1989 | Weinstein et al. | 128/207.17 |
| 5,069,206 | 12/1991 | Crosbie | 128/207.17 |
| 5,345,931 | 9/1994 | Battaglia | 128/207.17 |
| 5,402,776 | 4/1995 | Islava | 128/207.17 |
| 5,413,095 | 5/1995 | Weaver | 128/200.26 |
| 5,419,319 | 5/1995 | Werner | 128/207.17 |
| 5,490,504 | 2/1996 | Vrona et al. | 128/207.17 |
| 5,513,633 | 5/1996 | Islava | 128/207.17 |
| 5,575,282 | 11/1996 | Knoch et al. | 128/204.18 |

Primary Examiner—John G. Weiss
Assistant Examiner—William J. Deane, Jr.
Attorney, Agent, or Firm—Swanson & Bratschun LLC

[57] ABSTRACT

An endotracheal tube stabilizer includes an elongate frame having a transverse tube channel with an opening sized to radially receive an endotracheal tube. Straps are provided for securing the frame to the head of a patient with the frame bridging and the tube adjacent to the patient's mouth. A clamp has a body and a distal foot. The clamp body is attached to the frame with the distal foot traveling in a arcuate path relative to the frame from an open position remote from the opening of the transverse tube channel to a select operative position blocking the opening of the tube channel. In this manner, with an endotracheal tube received in the channel, the distal foot, when in an operative position, clamps the endotracheal tube in fixed position relative to the frame within the slot.

14 Claims, 4 Drawing Sheets

ENDOTRACHEAL TUBE STABILIZER

BACKGROUND

1. Field of Invention

This invention relates generally to endotracheal tube holders, particularly holders which stabilize breathing tubes within a patient's trachea.

2. Description of Prior Art

Endotracheal tubes (also referred to as breathing tubes) are well known in the medical arts for use in ventilation of patient's during administration of anesthesia, resuscitation, and other critical care intervention. The endotracheal tube passes between the patient's lips and teeth into the mouth, and comes to rest in the patient's trachea. The anatomical landmarks hereinafter referred to as the patient's airway include the mouth, oral pharynx, larynx, and trachea. Ensuring static stability of the endotracheal tube after initial placement is essential to quality patient care.

Problems resulting from endotracheal tubes becoming dislodged after initial placement have been well documented in the art.

Providing a suitable means for stabilizing the endotracheal tube has been the object of several prior art devices, including adhesive tape strips fastened from the tube to the patient's cheeks. Adhesive tape is well known for causing skin irritation and has fallen out of favor with the medical community. The evolution of tube securing devices include head encircling narrow fabric bands which require hand tying or Velcro™ type fasteners. A major draw-back to these band retention devices is the lack of grip necessary to hold the tube in place. Other types of tube holding devices are comprised of a face plate and integral bite block held against the patient's lips with an adjustable head strap. These face plate designs commonly include a tube locking mechanism, that prevents the tube from rotating out of position. Typical of these prior art tube holders are those disclosed in U.S. Pat. Nos. 4,249,529, 4,744,358, and 5,402,776.

The designs embodied in prior art tube holder devices have been cumbersome and complicated. Most tube holders accommodate a narrow range of tube sizes and provide limited access to the patient's mouth. Installation of the harness or attachment system of most tube holders requires multiple steps.

SUMMARY OF THE INVENTION

In a first embodiment an endotracheal tube stabilizer includes an elongate frame having a transverse tube channel with an opening sized to receive an endotracheal tube. Straps are provided for securing the frame to the head of a patient with the frame bridging and the tube channel adjacent to the patient's mouth. A clamp having a body and a distal foot is attached by the clamp body to the frame with the distal foot traveling in an arcuate path relative to the frame from an open position remote from the opening of the transverse tube channel to a select operative position blocking the opening of the tube channel, whereby with an endotracheal tube received in the slot the distal foot, in the operative position, clamps the endotracheal tube in a fixed position relative to the frame within the channel. Preferably, an arcuate track is attached to the frame with the clamp body slidably engaging the arcuate track. Serrations are provided on a surface of the arcuate track. A blade extends from the clamp body and is biased to an extended position in operative engagement with the serrations to secure the clamp body against movement along the arcuate track. The blade is retractable to a retracted position out of engagement with the serrations to enable free movement of the clamp body along the track. Preferably, the serrations are inclined to allow free movement of the clamp body toward the mouth of the tube channel with the blade in the extended position while preventing movement of the clamp body away from the mouth with the blade is in the extended position. A lever extends from the frame and is spaced from the arcuate track so that a clinician can engage the lever and the clamp body between a finger and a thumb of one hand and slide the clamp body toward the lever to secure an endotracheal tube within the channel.

In another embodiment an endotracheal tube stabilizer includes an elongate frame having an transverse tube channel with an opening sized to radially receive an endotracheal tube and an elongate track attached to the frame proximate the tube channel. Straps are provided for securing the frame to the head of a patient with the frame bridging and the tube channel adjacent the patient's mouth. A clamp having a body and a distal foot slidably engages the frame track at the clamp body and is freely slidable in a direction from an open position with the foot remote from the opening of the tube channel toward an operative position with the foot blocking the opening of the tube channel. Serrations on a surface of the track and a cooperating blade extending from the clamp body prevent slidable movement of the clamp body in a direction from the operative position toward the open position without manual actuation of the blade to a retracted position.

Yet another embodiment of the endotracheal tube stabilizer is an elongate frame having a transverse tube channel with an opening sized to radially receive an endotracheal tube. A clamp having a body and a distal foot is attached at the body to the frame for movement of the distal foot between an operative position with the foot blocking the opening of the tube channel and an open position with the foot remote from the opening of the tube channel. A ratchet structure between the clamp body and the frame permits free movement of the distal foot toward the operative position and prevents movement of the distal foot in a direction toward the open position without manual actuation.

The endotracheal tube stabilizer of the present invention provides a simple, reliable and rapid apparatus for locking an endotracheal tube securely in a select position relative to a patient's airway. The endotracheal tube stabilizer provides a rachet clamp actuated by a single hand clasping motion which secures the endotracheal tube where desired. The arcuate motion of the clamp foot enables the tube stabilizer to readily accommodate a wider range of tube sizes than prior art devices. Moreover, the endotracheal tube stabilizer is molded from thermoplastic in a shape conforming to the contours of a person's mouth. This not only enhances the comfort of a user, it provides for simple and inexpensive manufacture of the frame. The clamp can be readily disengaged from the tube stabilizer by the single hand of a clinician facilitating ready readjustment of the position of the endotracheal tube should such readjustment become necessary by patient movement. The endotracheal tube stabilizer further provides an arcuate wall extending lengthwise into a patient's mouth to protect the tube from pinching by a patient's teeth. Finally, the endotracheal tube stabilizer provides apertures on opposite sides of the tube channel which promote clinician access to a patient's mouth.

DETAILED DESCRIPTION OF THE PREFERRED EMBODIMENT

Figure 1:
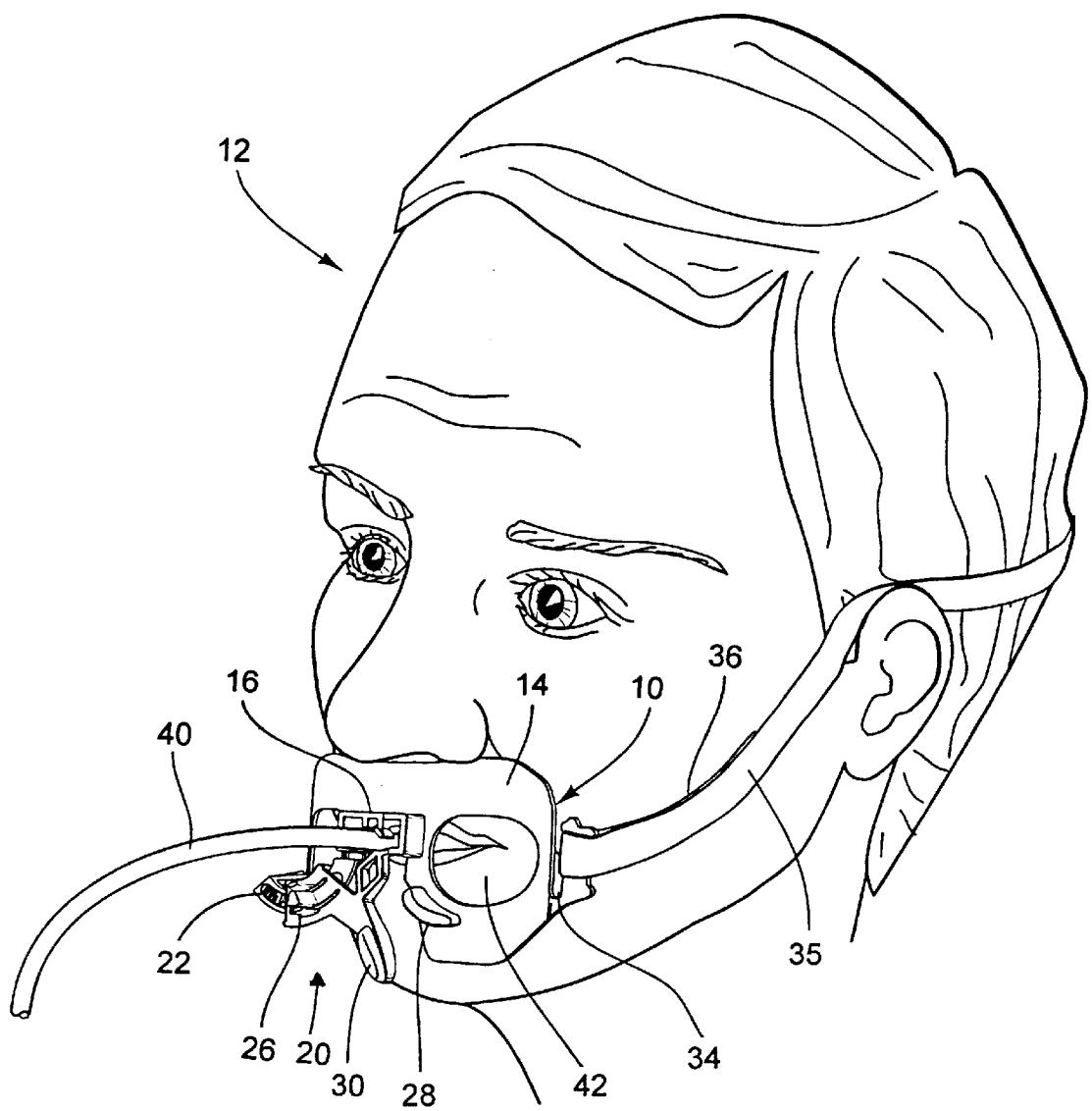
FIG. 1 is a pictorial view of a functioning endotracheal tube stabilizer of the present invention which shows how the stabilizer maintains an endotracheal tube in its correct position inside a patient's airway.
Figure 2:
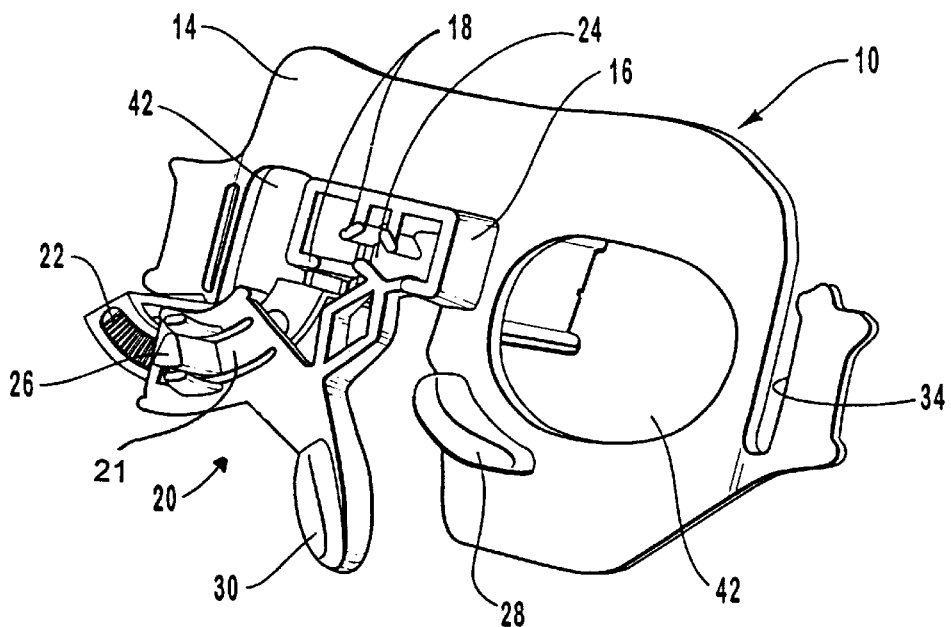
FIG. 2 is a perspective view of the endotracheal tube stabilizer of FIG. 1.

The endotracheal tube stabilizer of the current invention is illustrated in FIG. 2. The function of the tube stabilizer 10 is illustrated in FIG. 1 as it would be typically applied to a patient 12 in order to stabilize an endotracheal tube 40. The tube stabilizer 10 is held in place within the patient's airway by means of a fastening strap 35 as illustrated in FIG. 1.

Referring to FIGS. 1–8 of the drawings, the tube stabilizer is constructed of two separate yet interactive components, hereinafter referred to as the frame assembly 14 and the ratchet clamp assembly 20. Both the frame assembly 14, and the ratchet clamp assembly 20 consist of multiple sub-components, the combination of which makes up the tube stabilizer 10.

The frame assembly 14 illustrated in the preferred embodiment FIG. 2 is formed from a single piece of suitable plastic material that has the general appearance of eye glasses. The frame assembly is shaped to fit over the contours of the human face, and is held against the mouth with a fastening strap 35 as illustrated in FIG. 1.

Figure 3:
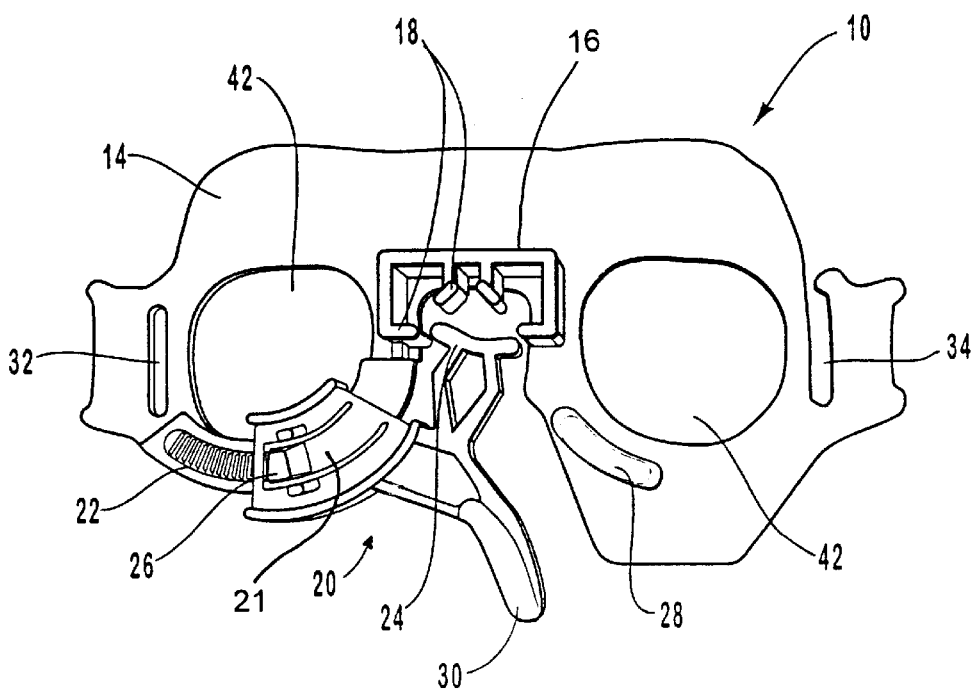
FIG. 3 is a front elevation view of the endotracheal tube stabilizer of FIG. 1.
Figure 4:
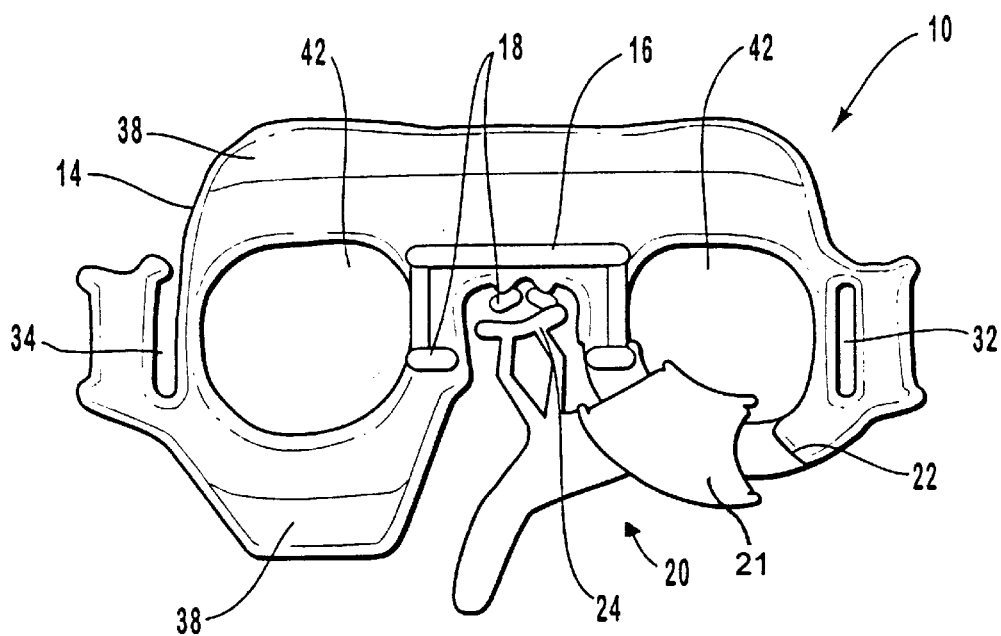
FIG. 4 is a rear elevation view of the endotracheal tube stabilizer of FIG. 1.
Figure 5:
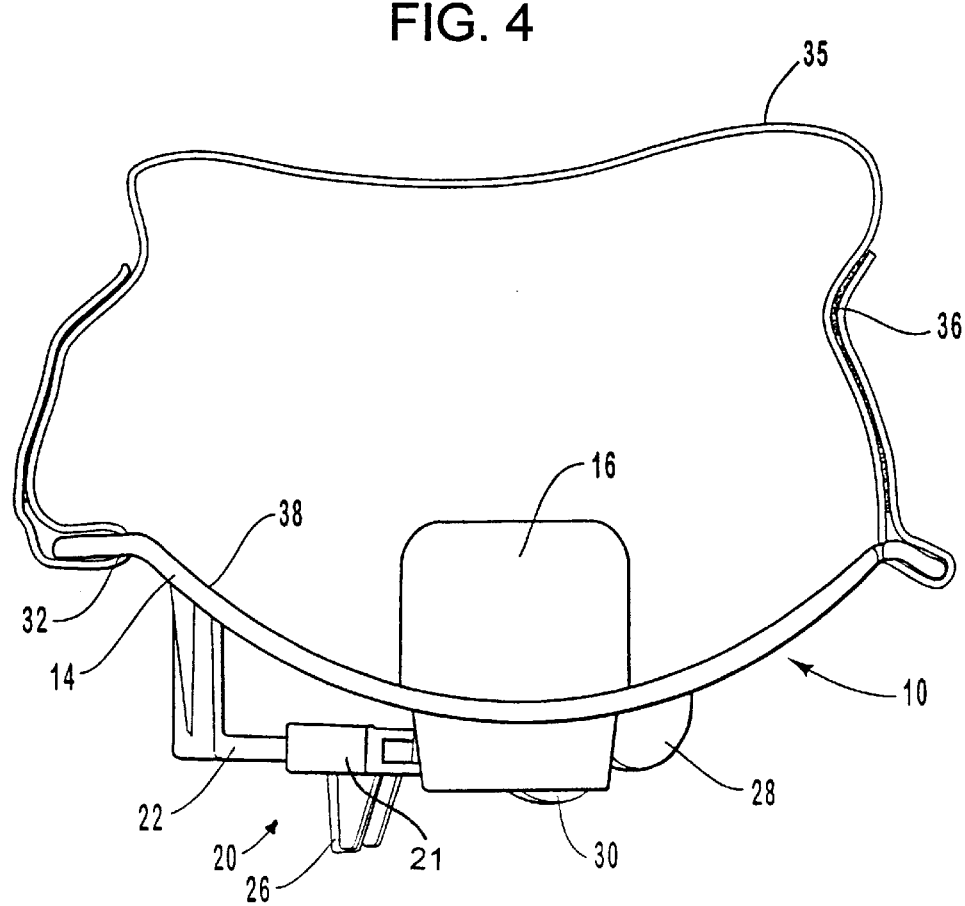
FIG. 5 is a top plan view of the endotracheal tube stabilizer of FIG. 1.

Integral to frame assembly 14 is tube channel 16 which projects along a perpendicular axis from the center of frame assembly 14 as illustrated in FIGS. 3–5. Tube channel 16 projects out from both the front and back of frame assembly 14. Integral to tube channel 16 on the inside surface are channel runners 18 which protrude from the interior wall of channel 16 in a parallel orientation as illustrated in FIGS. 2,3,4, and 6.

Adjacent to tube channel 16 on both left and right sides are two elliptical shaped openings, apertures 42, as seen in FIGS. 1,2,3,4,7 and 8.

Integral elements of frame assembly 14 are left strap slot 32 and right strap slot 34 located at opposite ends of frame assembly 14, as illustrated in FIGS. 1–4.

In FIG. 1 fastening strap 35 is shown pre-attached to left strap slot 32 and passes around the back of the head and neck of patient 12, it then terminates in right strap slot 34, which is open at the top for rapid placement of fastening strap 35.

Figure 6:
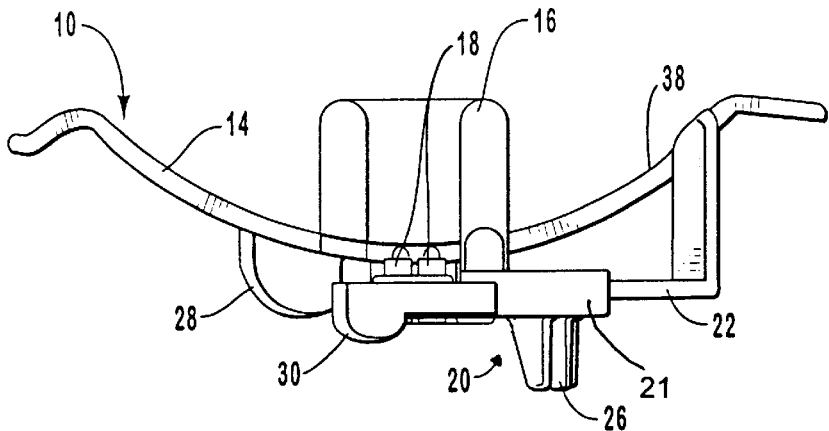
FIG. 6 is a bottom plan view of the endotracheal tube stabilizer of FIG. 1.

Along the bottom left radius of frame assembly 14 is serrated ratchet track 22 which is integral to frame assembly 14 and is elevated from the concave plane of frame assembly 14. This is best illustrated in FIGS. 5,6, and 7.

Serrated ratchet track 22 cooperates with the body 21 of the ratchet clamp assembly 20 to form a clamping mechanism as shown in FIGS. 2,3,5,6, and 7.

Figure 7:
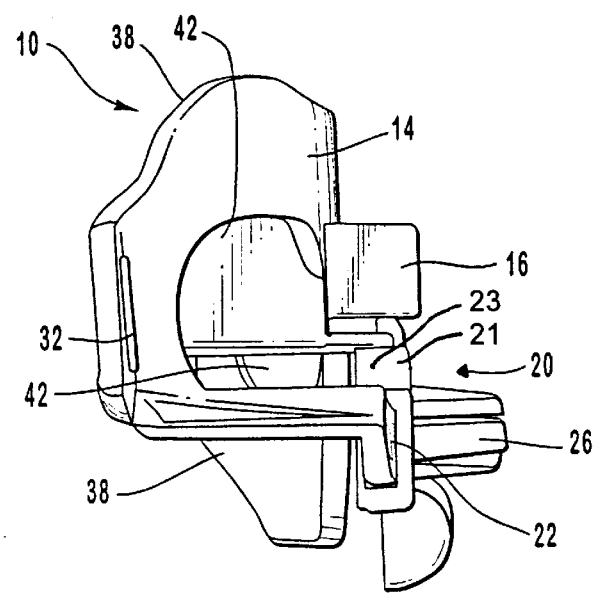
FIG. 7 is a left side elevation view of the endotracheal tube stabilizer of FIG. 1.
Figure 8:
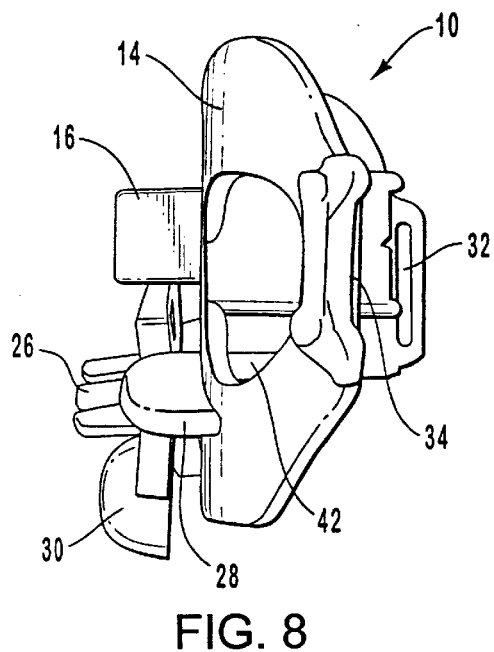
FIG. 8 is a right side elevation view of the endotracheal tube stabilizer of FIG. 1.

Ratchet clamp assembly 20 is molded from a crescent shaped flexible plastic material and is permanently affixed to serrated ratchet track 22 by means of a wrap-around living hinge 23 (see FIG. 7). As illustrated in the preferred embodiment FIG. 2, the ratchet clamp assembly 20 travels freely from left to right along serrated ratchet track 22. As illustrated in FIG. 3 the ratchet clamp assembly 20 is comprised of a clamping foot 24, a thumb lever 30, and a ratchet release lever 26 having a beveled blade (not shown) at its distal end which engages the ratchet track 22.

Along the bottom right radius of frame assembly 14 adjacent to tube channel 16 is finger brace 28, which extends out on a right angle from the outside edge of frame assembly 14 as shown in the preferred embodiment FIG. 2.

Referring to FIG. 5, fastening strap 35 is comprised of a brushed nylon fabric band of a suitable length allowing for adjustability to the patient's head and neck circumference. Integral to both ends of fastening strap 35 is hook fastener 36.

In FIG. 4 foam pads 38 are attached to the inside surfaces of frame assembly 14 by means of an integral pressure sensitive adhesive.

The endotracheal tube stabilizer 10 is positioned over a patient's mouth where an endotracheal tube 40 extends from the patient's mouth as shown in FIG. 1. Endotracheal tube 40 is placed inside tube channel 16 so as not to disturb correct placement of endotracheal tube 40, usually by sliding it radially therein.

With endotracheal tube 40 inside tube channel 16, tube channel 16 is then advanced between the patient's teeth creating a conduit which protects the endotracheal tube from the clamping pressure of the patient's teeth.

As was previously described, one end of fastening strap 35 is pre-attached to strap slot 32 by means of an interlocking section of hook fastener 36. The other end of fastening strap 35 remains loose while it is positioned behind the patient's head or neck. The loose end of fastening strap 35 is slid into the open strap slot 34. Fastening strap 35 is then pulled taut and locked in place with hook fastener 36. As endotracheal tube stabilizer 10 is pulled snug against a patient's mouth, foam pads 38 provide a cushion between frame assembly 14 and the patient's mouth.

With endotracheal tube stabilizer 10 secured to patient 12 as shown in FIG. 1, the forgoing steps will secure endotracheal tube 40 to endotracheal tube stabilizer 10.

Endotracheal tube 40 is locked into endotracheal tube stabilizer 10 by engaging the ratchet clamp mechanism. The ratchet clamp mechanism is comprised of ratchet clamp assembly 20 which is integral to thumb lever 30 and clamping foot 24. By grasping finger brace 28 and thumb lever 30 with finger and thumb respectively and squeezing together, clamping foot 24 forces endotracheal tube 40 snugly inside tube channel 16 as shown in FIG. 1. As thumb lever 30 and finger brace 28 are squeezed together, ratchet clamp assembly 20 travels along serrated ratchet track 22. Integral to ratchet clamp assembly 20 is ratchet release lever 26 which comprises a beveled blade that engages the slanted teeth on serrated ratchet track 22 in such a way as to provide incremental unidirectional movement of ratchet clamp assembly 20 along serrated ratchet track 22. Adjusting or releasing ratchet clamp assembly 20 is accomplished by lifting up on ratchet release lever 26.

It should be noted that access to the patient's mouth is available during and after installation of endotracheal tube stabilizer 10 via apertures 42.

The subject invention, is comprised of a frame assembly 14 which is shaped to fit over the contours of a person's mouth; the invention has the general appearance of spectacles. Cooperating with the lower left radius of frame assembly 14 is ratchet clamp assembly 20. The ratchet clamp assembly 20 provides pressure to secure endotracheal tube 40 inside tube channel 16 which is integral to frame assembly 14. Tube channel 16 extends inbetween the patient's front teeth to insure placement and integrity of the endotracheal tube. The endotracheal tube stabilizer is secured to the patient by means of an adjustable fastening strap 35. Access to both sides of the patient's mouth is achieved with apertures 42 which are integral to frame assembly 14.

In the preferred embodiment the overall dimensions of the endotracheal tube stabilizer are approximately 100 mm wide and approximately 50 mm high, with a depth of approximately 35 mm. The wall thickness of the frame assembly is approximately 3 mm. The fastening strap 35 is approximately 600 mm long, 15 mm wide, and 5 mm thick. Apertures 42 have an inside diameter of approximately 35 mm. Tube channel 16 has an inside width of approximately 16 mm, and will accommodate endotracheal tube sizes 3 mm to 10 mm.

Suitable construction materials for the endotracheal tube stabilizer include polypropylenes, thermal plastic rubber, and any other deformable plastics which are durable and hold their original configuration over time. Moreover, the endotracheal tube stabilizer accommodates a wide range of patients and endotracheal tube sizes. The ratchet clamping mechanism and quick fastening strap allow the subject invention to be applied in four simple steps. Unlike prior art inventions that inhibit access to a patient's mouth the subject invention provides access to both sides of a patient's mouth.

Although the preceding description contains specifications particular to the subject invention, these should not be construed as limiting the scope of this invention, but as merely providing illustrations of some of the presently preferred embodiments of the invention.

Numerous modifications and variations of the subject invention are possible in light of the above teachings. Thus the scope of the subject invention should be determined by the appended claims and their legal equivalents, and not according to the examples given.

I claim:

1. An endotracheal tube stabilizer comprising:
   an elongate frame having a transverse tube channel with an opening sized to radially receive an endotracheal tube;
   means for securing the elongate frame to the head of a patient with the elongate frame bridging and the tube channel adjacent to the patient's mouth; and
   a clamp having a body and a distal foot, the clamp body being attached to the elongate frame with the distal foot traveling in an arcuate path relative to the elongate frame from an open position remote from the opening of the transverse tube channel to a select operative position blocking the opening of the tube channel, whereby with an endotracheal tube received in the channel the distal foot, in the operative position, clamps the endotracheal tube in a fixed position relative to the elongate frame within the tube channel.

2. The endotracheal tube stabilizer of claim 1 wherein the elongate frame further comprises a pair of apertures on opposite sides of the tube channel, whereby, with the elongate frame secured to the head of a patient, a clinician can access the mouth of the patient from opposite sides of the tube channel.

3. The endotracheal tube stabilizer of claim 1 wherein the elongate frame has a lengthwise concave contour.

4. The endotracheal tube stabilizer of claim 1 further comprising an arcuate wall extending lengthwise essentially normally from the elongate frame about the tube channel periphery defining a protective jacket for an endotracheal tube received in the tube channel.

5. The endotracheal tube stabilizer of claim 4 further comprising a plurality of runners extending lengthwise of and inwardly from the wall.

6. The endotracheal tube stabilizer of claim 1 further comprising an arcuate track attached to the elongate frame with the clamp body slidably engaging the arcuate track.

7. The endotracheal tube of claim 6 further comprising serrations on a surface of the arcuate track and a blade extending from the clamp body biased to an extended position in operative engagement with the serrations to secure the clamp body against movement along the arcuate track, the blade being retractable to a retracted position out of engagement with the serrations to enable free movement of the clamp body along the arcuate track.

8. The endotracheal tube stabilizer of claim 7 wherein the serrations are inclined to allow free movement of the clamp body toward the mouth of the tube channel with the blade in the extended position while preventing movement of the clamp body away from the mouth with the blade in the extended position.

9. The endotracheal tube stabilizer of claim 6 further comprising a lever extending from the elongate frame spaced from the arcuate track, the lever being disposed so that a clinician can engage the lever and clamp body between a finger and thumb of one hand and slide the clamp body toward the lever.

10. The endotracheal tube stabilizer of claim 6 wherein the arcuate track is elevated relative to the elongate frame.

11. An endotracheal tube stabilizer comprising:
    an elongate frame having a transverse tube channel with an opening sized to radially receive an endotracheal tube and an elongate track attached to the elongate frame proximate the tube channel;
    means for securing the elongate frame to the head of a patient with the elongate frame bridging and the tube channel adjacent to the patient's mouth;
    a clamp having a body and a distal foot, the clamp body slidably engaging the elongate track and being freely slidable in a direction from an open position with the foot remote from the opening of the tube channel toward an operative position with the foot blocking the opening of the tube channel; and
    locking means between the track and the clamp body for preventing slidable movement of the clamp body in a direction from the operative position toward the open position without manual actuation.

12. The endotracheal tube stabilizer of claim 11 wherein the locking means comprises serrations on a surface of the elongate track and a blade extending from the clamp body, the blade being biased to an extended position in operative engagement with the serrations to lock the clamp body against movement in a direction from the operative position toward the open position and the blade being manually retractable to a retracted position out of operative engagement with the serrations to enable movement of the clamp body in a direction from the operative position toward the open position.

13. The endotracheal stabilizer of claim 11 further comprising a lever extending forward of the elongate frame and spaced from the elongate track, the lever being disposed so that a clinician can engage the lever and clamp body between a finger and thumb of one hand and slide the clamp body in the direction toward the operative position.

14. An endotracheal tube stabilizer comprising:

an elongate frame having a transverse tube channel with an opening sized to radially receive an endotracheal tube;

a clamp having a body and a distal foot with the body attached to the elongate frame for movement of the distal foot between an operative position with the foot blocking the opening of the tube channel and an open position with the foot remote from the opening of the tube channel; and means between the clamp body and the elongate frame for permitting free movement of the distal foot toward the operative position and for preventing movement of the distal foot in a direction toward the open position without manual actuation.

* * * * *